(12) United States Patent
Svendsen (10) Patent No.: US 6,811,142 B2
(45) Date of Patent: Nov. 2, 2004

(54) VALVE DEVICE (75) Inventor: Gunnar N. Svendsen, Jyllinge (DK)

(73) Assignee: Unomedical A/S (DK)

( * ) Notice: Subject to any disclaimer, the term of this patent is extended or adjusted under 35 U.S.C. 154(b) by 117 days.

(21) Appl. No.: 10/240,882

(22) PCT Filed: Apr. 5, 2001

(86) PCT No.: PCT/DK01/00232
§ 371 (c)(1),
(2), (4) Date: Oct. 4, 2002

(87) PCT Pub. No.: WO01/76673
PCT Pub. Date: Oct. 18, 2001

(65) Prior Publication Data
US 2003/0047704 A1 Mar. 13, 2003

(30) Foreign Application Priority Data
Apr. 6, 2000 (DK) .................................. 2000 00581

(51) Int. Cl.[7] .............................................. F16K 31/00
(52) U.S. Cl. ..................... 251/335.2; 251/321; 251/331
(58) Field of Search .......................... 251/335.2, 335.1, 251/335.3, 340, 320, 321, 331

(56) References Cited

U.S. PATENT DOCUMENTS

| 2,579,982 | A | * | 12/1951 | Arthur ......................... 251/331 |
| 2,605,991 | A | * | 8/1952 | Kaye ........................... 251/331 |
| 3,469,582 | A | | 9/1969 | Jackson |
| 3,517,669 | A | | 6/1970 | Buono et al. |
| 3,595,445 | A | | 7/1971 | Buford et al. |
| 3,902,500 | A | | 9/1975 | Dryden |
| 3,958,566 | A | | 5/1976 | Furihata |
| 3,991,762 | A | | 11/1976 | Radford |
| 4,072,292 | A | * | 2/1978 | Banon ......................... 251/331 |
| 4,180,066 | A | | 12/1979 | Milliken et al. |
| 4,266,815 | A | | 5/1981 | Cross |

(List continued on next page.)

FOREIGN PATENT DOCUMENTS

| EP | 0349745 A1 | 1/1990 | |
| EP | 0 434 598 A1 | * | 6/1991 | ................. 251/340 |
| EP | 1208865 A2 | 5/2002 | |
| EP | 1210957 A1 | 6/2002 | |
| FR | 2 682 603 A | 10/1991 | |
| GB | 2123106 A | 1/1984 | |
| GB | 2 207 736 B | 4/1988 | |
| GB | 2270845 A | 3/1994 | |
| WO | WO 90/14539 | 11/1990 | |
| WO | WO 93/17742 A1 | 9/1993 | |
| WO | WO 93/21981 A2 | 11/1993 | |
| WO | WO 95/31240 A1 | 11/1995 | |
| WO | WO 95/31250 A1 | 11/1995 | |
| WO | WO 96/09082 A1 | 3/1996 | |
| WO | WO 96/26757 A1 | 9/1996 | |
| WO | WO 96/30069 A1 | 10/1996 | |
| WO | WO 98/10808 A2 | 3/1998 | |

Primary Examiner—J. Casimer Jacyna
(74) Attorney, Agent, or Firm—Finnegan, Henderson, Farabow, Garrett and Dunner LLP (57) ABSTRACT A valve device (200) for a closed system for endotracheal aspiration of a patient via a catheter. The device (200) comprises a valve chamber (220, 222) that can be connected to a vacuum source and to the catheter, a valve body (250) arranged in the valve chamber (220, 222), a manually operated actuator button (210) for the valve body (215), a coupling (260) engaging the valve body (250) and to the actuator button (210) for transmitting a movement of the actuator button (210) to the valve button (250), a spring device for holding the valve body (250) in the first position. The device is characterised in that the wall (216) that delimits the valve chamber (220, 222) comprises an opening (219) for receiving the valve body (250), that a resilient membrane (253) forms a sealing of the opening (219) within the valve housing (215), that the resilient membrane is connected to the valve body and the valve housing (215), respectively, and that the coupling (260) extends exteriorly relative to the valve housing (215).

12 Claims, 5 Drawing Sheets

U.S. PATENT DOCUMENTS

| | | |
|---|---|---|
| 4,287,889 A | 9/1981 | Stupar |
| 4,452,473 A | 6/1984 | Ruschke |
| 4,510,933 A | 4/1985 | Wendt et al. |
| 4,534,542 A | 8/1985 | Russo |
| 4,537,182 A | 8/1985 | Otani |
| 4,561,428 A | 12/1985 | Konomura |
| 4,569,344 A * | 2/1986 | Palmer ................ 128/207.16 |
| 4,610,664 A | 9/1986 | Harle |
| 4,638,539 A | 1/1987 | Palmer |
| 4,673,393 A | 6/1987 | Suzuki et al. |
| 4,696,296 A | 9/1987 | Palmer |
| 4,722,366 A | 2/1988 | Maaskamp |
| 4,735,441 A | 4/1988 | Stephens |
| 4,825,859 A | 5/1989 | Lambert |
| 4,834,726 A | 5/1989 | Lambert |
| 4,836,199 A | 6/1989 | Palmer |
| 4,838,255 A | 6/1989 | Lambert |
| 4,846,167 A | 7/1989 | Tibbals |
| 4,850,350 A | 7/1989 | Jackson |
| 4,867,153 A | 9/1989 | Lorenzen et al. |
| 4,872,579 A | 10/1989 | Palmer |
| 4,938,741 A | 7/1990 | Lambert |
| 4,967,743 A | 11/1990 | Lambert |
| 4,981,466 A | 1/1991 | Lumbert |
| 5,009,391 A | 4/1991 | Steigerwald |
| 5,025,806 A | 6/1991 | Palmer et al. |
| 5,060,646 A | 10/1991 | Page |
| 5,065,754 A | 11/1991 | Jensen |
| 5,073,164 A | 12/1991 | Hollister et al. |
| 5,083,561 A | 1/1992 | Russo |
| 5,083,750 A * | 1/1992 | Balik .................. 251/335.2 |
| 5,107,829 A | 4/1992 | Lambert |
| 5,116,088 A | 5/1992 | Bird |
| 5,120,305 A | 6/1992 | Boehringer et al. |
| 5,125,893 A | 6/1992 | Dryden |
| 5,133,345 A | 7/1992 | Lambert |
| 5,134,996 A | 8/1992 | Bell |
| 5,139,018 A | 8/1992 | Brodsky et al. |
| 5,140,983 A | 8/1992 | Jinotti |
| 5,158,569 A | 10/1992 | Strickland et al. |
| 5,163,926 A | 11/1992 | Bailey et al. |
| 5,181,908 A | 1/1993 | Bell |
| 5,184,611 A | 2/1993 | Turnbull |
| 5,215,522 A | 6/1993 | Page et al. |
| 5,220,916 A | 6/1993 | Russo |
| 5,254,098 A | 10/1993 | Ulrich et al. |
| 5,255,676 A | 10/1993 | Russo |
| 5,269,756 A | 12/1993 | Dryden |
| 5,269,768 A | 12/1993 | Cheung |
| 5,277,177 A | 1/1994 | Page et al. |
| 5,279,549 A | 1/1994 | Ranford |
| 5,300,043 A | 4/1994 | Devlin et al. |
| 5,309,902 A | 5/1994 | Kee et al. |
| 5,325,850 A | 7/1994 | Ulrich et al. |
| 5,325,851 A | 7/1994 | Reynolds et al. |
| 5,333,606 A | 8/1994 | Schneider et al. |
| 5,333,607 A | 8/1994 | Kee et al. |
| 5,335,655 A | 8/1994 | Kee |
| 5,337,780 A | 8/1994 | Kee |
| 5,343,857 A | 9/1994 | Schneider et al. |
| 5,349,950 A | 9/1994 | Ulrich et al. |
| 5,355,876 A | 10/1994 | Brodsky et al. |
| 5,368,017 A | 11/1994 | Sorenson et al. |
| 5,377,672 A | 1/1995 | Kee |
| 5,419,769 A | 5/1995 | Devlin et al. |
| 5,433,195 A | 7/1995 | Kee et al. |
| 5,445,141 A | 8/1995 | Kee et al. |
| 5,449,348 A | 9/1995 | Dryden |
| 5,456,675 A | 10/1995 | Wolbring et al. |
| 5,460,613 A | 10/1995 | Ulrich et al. |
| 5,490,503 A | 2/1996 | Hollister |
| 5,496,287 A | 3/1996 | Jinotti |
| 5,513,628 A | 5/1996 | Coles et al. |
| 5,562,618 A | 10/1996 | Cai et al. |
| 5,579,762 A | 12/1996 | Lee |
| 5,582,161 A | 12/1996 | Kee |
| 5,598,840 A | 2/1997 | Iund et al. |
| 5,611,336 A * | 3/1997 | Page et al. ............ 128/207.16 |
| 5,613,663 A | 3/1997 | Schmidt et al. |
| 5,628,306 A | 5/1997 | Kee |
| 5,632,729 A | 5/1997 | Cai et al. |
| 5,636,625 A | 6/1997 | Miyagi et al. |
| 5,642,726 A | 7/1997 | Owens et al. |
| 5,645,048 A | 7/1997 | Brodsky et al. |
| 5,664,564 A * | 9/1997 | Palmer ................ 128/205.19 |
| 5,664,594 A | 9/1997 | Kee |
| 5,669,380 A | 9/1997 | Garry et al. |
| 5,676,136 A | 10/1997 | Russo |
| 5,694,922 A | 12/1997 | Palmer |
| 5,702,374 A | 12/1997 | Johnson |
| 5,730,123 A | 3/1998 | Lorenzen et al. |
| 5,735,271 A | 4/1998 | Lorenzen et al. |
| 5,738,091 A | 4/1998 | Kee et al. |
| 5,775,325 A | 7/1998 | Russo |
| 5,779,687 A | 7/1998 | Bell et al. |
| 5,791,337 A | 8/1998 | Coles et al. |
| 5,794,986 A | 8/1998 | Gansel et al. |
| 5,827,218 A | 10/1998 | Nguyen et al. |
| 5,830,214 A | 11/1998 | Flom et al. |
| 5,855,562 A | 1/1999 | Moore et al. |
| 5,864,938 A | 2/1999 | Gansel et al. |
| 5,919,174 A | 7/1999 | Hanson |
| 5,993,437 A | 11/1999 | Raoz |
| 6,012,451 A | 1/2000 | Palmer |
| 6,045,119 A * | 4/2000 | Erb .................... 251/335.2 |
| 6,070,582 A | 6/2000 | Kee |
| 6,135,110 A | 10/2000 | Roy |
| 6,148,857 A | 11/2000 | West et al. |
| 6,190,372 B1 | 2/2001 | Racz |
| 6,227,200 B1 | 5/2001 | Crump et al. |
| 6,254,061 B1 | 7/2001 | Levine et al. |
| 6,254,589 B1 | 7/2001 | Raoz |
| 6,305,665 B1 * | 10/2001 | Coura et al. ............ 251/335.3 |
| 6,415,789 B1 | 7/2002 | Freitas et al. |
| 6,494,203 B1 | 12/2002 | Palmer |
| 6,505,814 B1 * | 1/2003 | Satou et al. ............. 251/331 |
| 6,543,451 B1 | 4/2003 | Crump et al. |
| 6,575,944 B1 | 6/2003 | McNary et al. |
| 6,588,425 B2 | 7/2003 | Rouns et al. |
| 6,588,427 B1 | 7/2003 | Carlsen et al. |
| 6,602,219 B2 | 8/2003 | Madsen et al. |
| 6,609,520 B1 | 8/2003 | Carlsen et al. |
| 6,648,006 B1 * | 11/2003 | Ostergaard ............ 251/335.2 |
| 2001/0029953 A1 | 10/2001 | Neto et al. |
| 2001/0044600 A1 | 11/2001 | Elkins |
| 2003/0047704 A1 | 3/2003 | Svendsen |
| 2003/0056787 A1 | 3/2003 | Svendsen |
| 2003/0106558 A1 | 6/2003 | Cardon |
| 2003/0106559 A1 | 6/2003 | Svendsen |

\* cited by examiner

VALVE DEVICE

FIELD

The present invention relates to a valve device for a closed system for endotracheal aspiration of a patient via a catheter.

BACKGROUND

It is already known within the art to provide valve devices that are configured especially for use in systems for endotracheal aspiration of a patient. In this context reference is made to e.g. GB patent No 2,207,736, U.S. Pat. No. 4,569,344 and FR patent application No 2,682,603. These disclosures are incorporated in this application text by the present reference.

Albeit the prior art valve devices comply with a large number of the current requirements to functionality, they are, however, all associated with inconveniences. These are not only ascribed to high costs of manufacture, but also to constructive deficiencies that can, in some situations, reduce the performance of the valve devices. In the prior art valve devices, secretion sucked from the patient may thus deposit on the valve body as such, which may lead to sealing problems when the connection to the vacuum source is interrupted. Thus, adverse accumulation of secretion in the valve house interior may also occur.

The invention aims to provide a valve device that is superior to the known valve devices and that does not aim to remedy the described problems only, but can also be assembled in a relatively simple operation by use of a small number of components.

BRIEF SUMMARY

An improved valve device is obtained by the valve device described herein. Thus, by the invention the valve chamber has substantially no movable surfaces in the flow path for fluid that is aspired from the patient. When through-flow is permitted by manipulating the actuator button, the coupling that connects the valve body with the actuator button is withdrawn from the flow path, contrary to the devices disclosed in the above references.

In various embodiments, a device is provided that is simple to operate, a downward pressure on the actuator button in a direction towards the valve chamber causing a corresponding downward movement of the valve body and thereby opening the flow passage through the valve chamber.

In various embodiments, the valve device is conveniently enclosed in an actuator housing that has a face that enables the user of the device to provide a reaction force against the downward pressure force exerted on the actuator button.

Preferably, the flexible membrane that seals the opening for receipt of the valve body has resilient properties and may thus constitute the resilient member for controlling the movement of the valve body. The flexible membrane can particularly advantageously constitute an integral portion of the valve body. Besides, the valve body can particularly advantageously comprise engagement means that allow direct attachment to the coupling means via complementary engagement means configured on the coupling means.

Additional embodiments of the valve device enable auto-sealing properties, since a sub-atmospheric pressure from the vacuum source will merely entail an increased impact force between the valve body and the valve seat when the actuator button is in its first position in which the two flow passages are cut off from each other.

DRAWINGS

The invention will now be explained in further detail with reference to the embodiments shown in the drawings.

DESCRIPTION OF VARIOUS EMBODIMENTS

Figure 1:
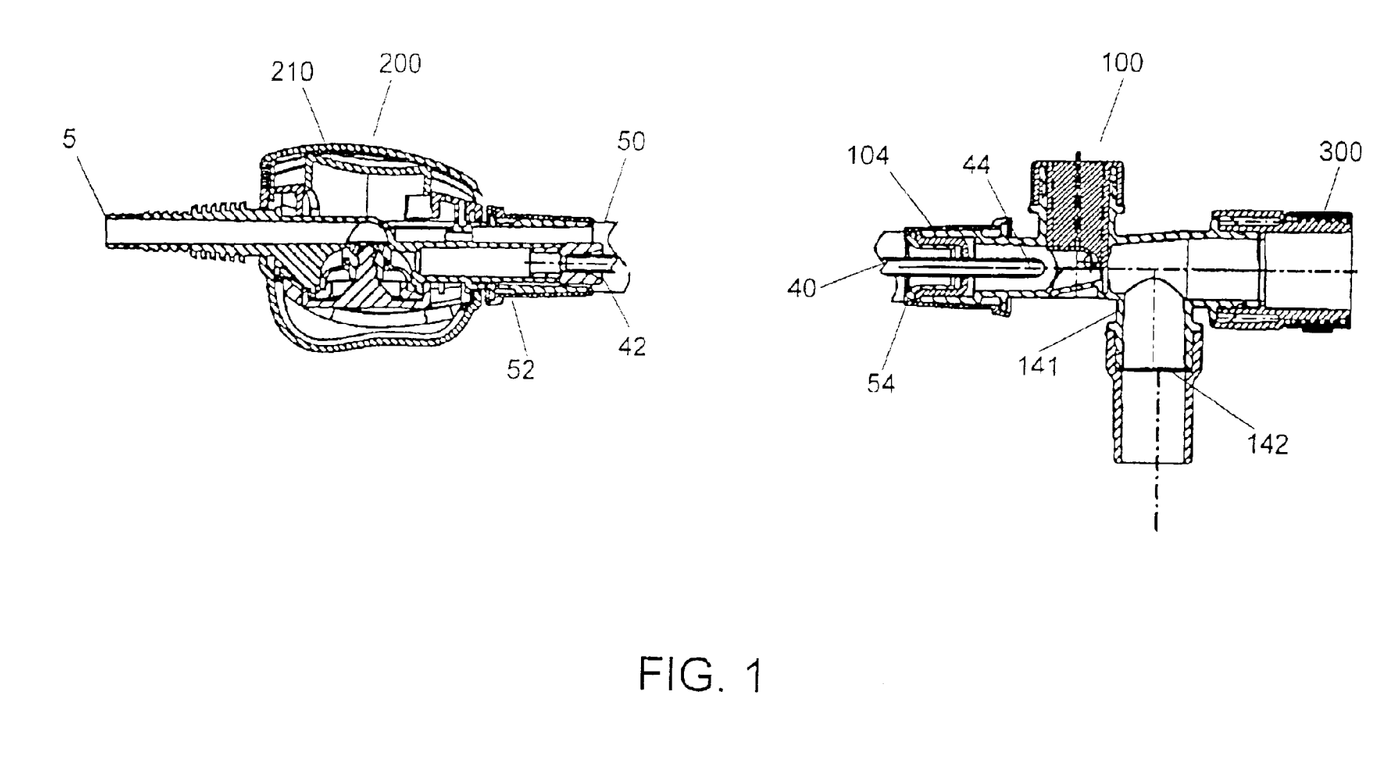
FIG. 1 illustrates a part of a system for endotracheal ventilation of a patient.

In principle, the functionality of the system shown in FIG. 1 corresponds to the functionality of e.g. the system described in DK patent application No 32/95. A flexible shrouding or pipe coupling 50 is, at its first end 52, connected to the valve device 200 according to the invention and it is, at its opposite end 54, connected to a manifold 100. To the left, the valve device 200 is configured for being connected to a not shown suction device for generating a sub-atmospheric pressure in the system 1. The manifold 100, which is preferably transparent, is also configured to be connected—via a coupling 300—to a tubular member or "tube" for endotracheal ventilation of a patient, ie a tubular member configured for being introduced into the respiratory tracts of the patient with a view to maintaining artificial ventilation of the patient. An opening 142 in a ventilation stub 141 allows ventilation of the patient by means of a not shown, conventional apparatus.

Besides, the system 1 conventionally comprises a catheter 40 that extends interiorly of the shrouding 50 and that can be introduced into the patient's respiratory tracts to draw out secretion. At its first end 42, the catheter 40 is securely connected to the valve device 200 and, at its opposite end 44, it is displaceably received in the manifold 100, the catheter being—via a packing 104—sealed relative to the shrouding 50 so as to prevent fluid from penetrating into the shrouding. Also, the packing 104 causes secretion to be scraped off the outside of the catheter 40 during withdrawal of the catheter from the patient. It will be understood that the opposite end 44 of the catheter forms a suction point that can, while the shrouding 50 is simultaneously folded, be displaced through the manifold interior and into the not shown tube for ventilation of the patient. By this movement the end 44 of the catheter is thus conveyed to the right in FIG. 1. Hereby it is possible to perform regular suction of secretion from the patient's respiratory tracts, as the operator connects the system 1 to the suction device by operating an actuator button 210 arranged in the valve device 200.

Figure 2:
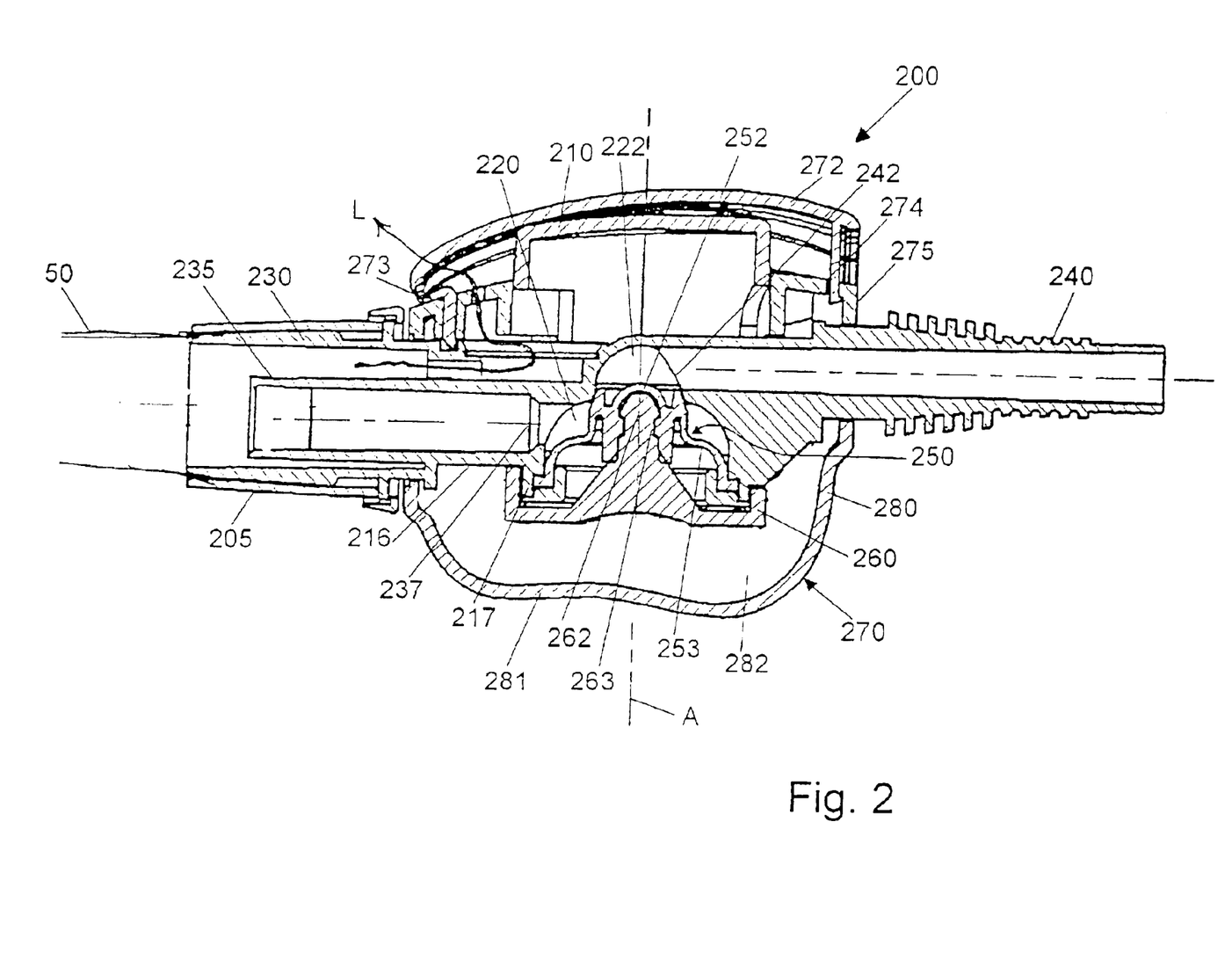
FIG. 2 illustrates a valve device according to the invention, seen in a cross-sectional view.

FIG. 2 is a more detailed view of the valve device 200 according to the invention. The valve device comprises an actuator housing that is generally designated by the reference numeral 270 and that has an interior cavity 282. From the actuator housing 270, a first cylindrical tubular member 235 extends and a second cylindrical tubular member 240 by which the valve device 200 can be connected to a suction catheter 40 and a not shown suction device, respectively. The first 235 and the second 240 tubular section define a first and a second flow passage, respectively, through the valve device 200 and the longitudinal axes of the tubular members are arranged to be mutually offset. The flow passages debouch in the valve device 200 interior into respective regions 237, 242. Around the first tubular member 235 a further, third tubular member 230 is arranged by which the valve device 200 can be connected to the above described shrouding 50.

More specifically the actuator housing 270 is defined by a wall 281 and has a lid portion 272 that is preferably transparent. The lid portion 272 has a hinge 273 whereby the lid portion 272 can turn to a position in which the user has access to an actuator button 210 arranged interiorly of the actuator housing 270. When the lid portion 272 is closed, it can be secured in engagement with the actuator housing 270 by means of barb-like means 274 and in this position it constitutes a visual indication that the valve device 200 is not in its suction state. By application of a downwardly oriented pressure, the actuator button 210 can be shifted from the shown position to a second position in which the flow passage is formed by the first tubular member 235 and the second tubular member 240, respectively, being caused to be in flow connection, as will be described more detailed.

The actuator housing 270 also comprises a valve housing that is arranged in the cavity 282 within the actuator housing 270 and that delimits an interior valve chamber consisting of a lower or first cavity 220 and an upper or second cavity 222. The valve housing which is identified by reference numeral 215 and which is seen best in FIG. 3, constitutes a separate part of the actuator housing 270, and the wall 216 of the valve housing 215 does not merely delimit the valve housing, but also said tubular members 230, 235 and 240. The tubular members 230, 235 and 240 extend, as shown, from the interior 282 of the actuator housing 270 via openings in the wall 281 of the actuator housing 270.

In the valve chamber a valve 250 is arranged for cutting off the flow connection between the first tubular member 235 and the second tubular member 240. The valve 250 is arranged in the lower cavity 220 within the valve housing and is biased so as to cut off the connection between the two tubular members 235, 240 in its normal position. To this end the valve 250 comprises a valve body 252 that has the shape of a pin with a downwardly open cavity and that cooperates with a valve seat 225 at the transition between the upper 222 and the lower 220 cavity, and a spring-like portion 253 that is configured for providing a biasing force by which the valve body 252 is kept in close abutment on the valve seat 225 in the normal position of the valve body 252. The valve body 252 and the spring-like portion 253 of the valve 250 are preferably made in one piece of a suitable plastics material. Via a coupling means 260 that extends outside the valve housing 215, the valve 250 is connected to the actuator button 210.

As shown, the coupling means 260 comprises a pin-like means 262 that is configured for being able to be secured in the downwardly open cavity within the valve body 252. To this end the pin-like means 262 has peripherally arranged engagement means 263 that co-operate with complementary engagement means arranged on the interior surface of the cavity interiorly of the valve body 252.

Besides, FIG. 2 shows how the cavity 220 combines with the further cavity 222 to form a flow passage that connects the first tubular member 235 to the second tubular member 240. It will appear that the further cavity 222 is arranged in extension of the cavity 220, along an axis A that extends perpendicular to the tubular members 235, 240. Both cavities are preferably rotational symmetrical about the axis A. When fluid flows through the valve device 200, that fluid will—following passage through the flow passage within the tubular member 235—be deflected in accordance with the axis A in order to subsequently flow on through the flow passage within the tubular member 240. With due regard to the terminology to be used below, the cavity 222 is to be understood as being situated at the upper or first side of the valve housing 215, whereas the cavity 220 is to be understood as being situated at the lower or other side of the valve housing 215.

Figure 3:
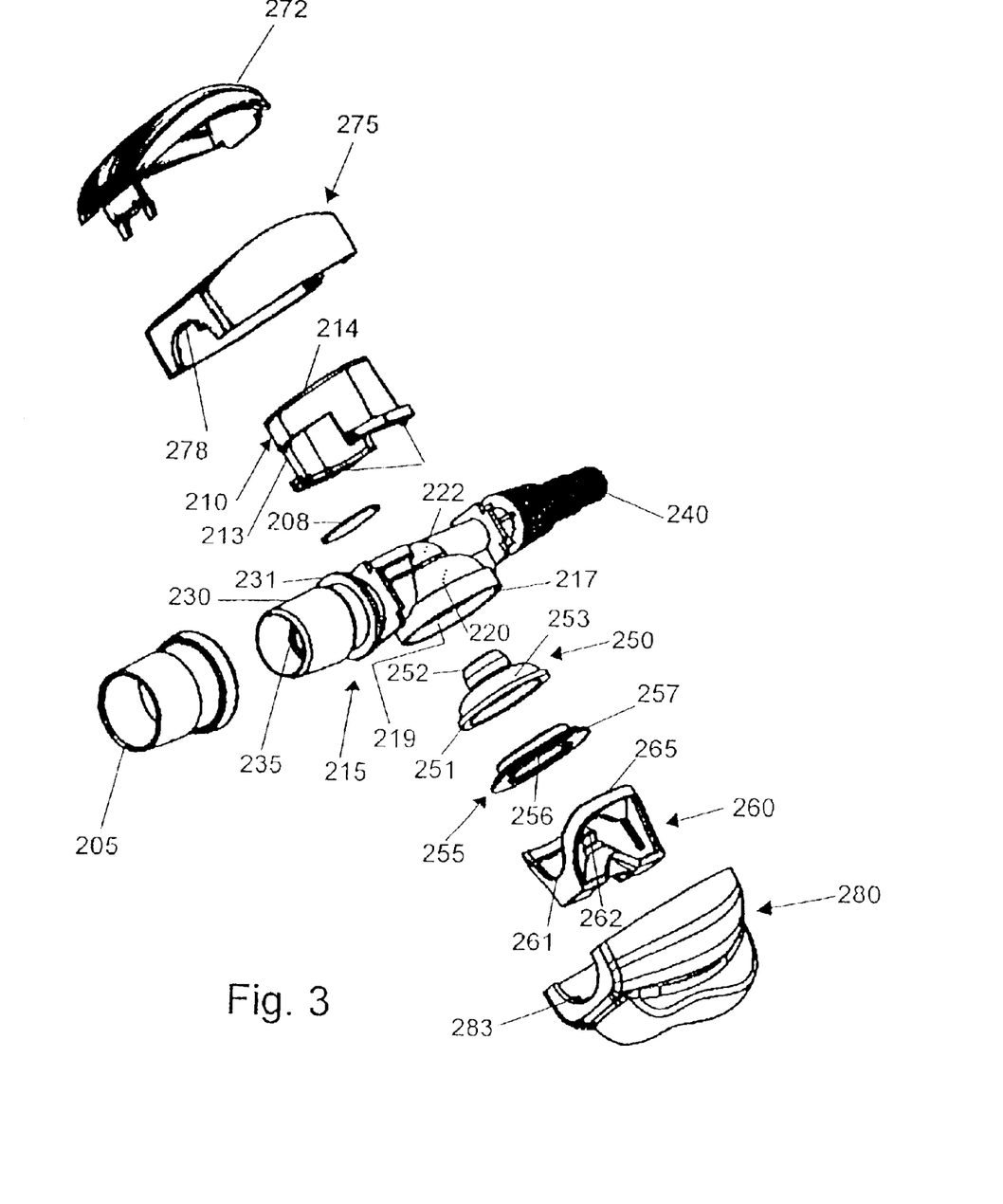
FIG. 3 illustrates the valve device shown in FIG. 2, in an exploded view.

In FIG. 3 the components that constitute the valve device 200 is shown prior to assembly. The reference numeral 215 designates the valve housing that is preferably manufactured as an integral unit. It will appear that the cavities 220, 222 within the valve housing 215 interior constitutes arched or domed portions of the valve housing 215. At the bottom, the cavity 220 has an opening 219 that is delimited by an annularly extending edge 217 that preferably extends in a plane perpendicular to the axis A. The opening 219 allows mounting of the valve 250.

It will appear from FIG. 3 that the valve body 252 has a pin-like shape, whereas a flexible, cup-shaped membrane that acts as a spring constitutes a further portion 253 of the valve 250. The flexible membrane 253 closes off the opening 219 within the valve housing 215, and the membrane is preferably secured to the edge 217 that delimits the opening 219 via an annular fixation body 255 that is welded to the edge 217 of the valve housing 215 and an annular edge 251 on the valve 250, respectively. FIG. 3 also shows the coupling means 260 that connects the actuator button 210 to the valve body 250. The coupling means 260 comprises an engagement face 265 that enables the coupling means 260 to cooperate with the actuator button 210.

It will also appear from FIG. 3 how, advantageously, the actuator housing 270 can be made of two halves 275, 280 that are configured for being assembled. In their assembled state, the two halves 275, 280 constitute an enclosure around the valve housing 215 with the actuator button 210 being in abutment on the coupling means 260 that is engaging the valve body 250 that is, in turn, closely connected to the valve housing 215. The upper half 275 has a cut-out that enables the user to obtain access to the actuator button 210. The actuator button 210 as well as the coupling means 260 is provided with recesses with respective bottom edges 213, 261, the object of which will appear from the below teachings.

Figure 4:
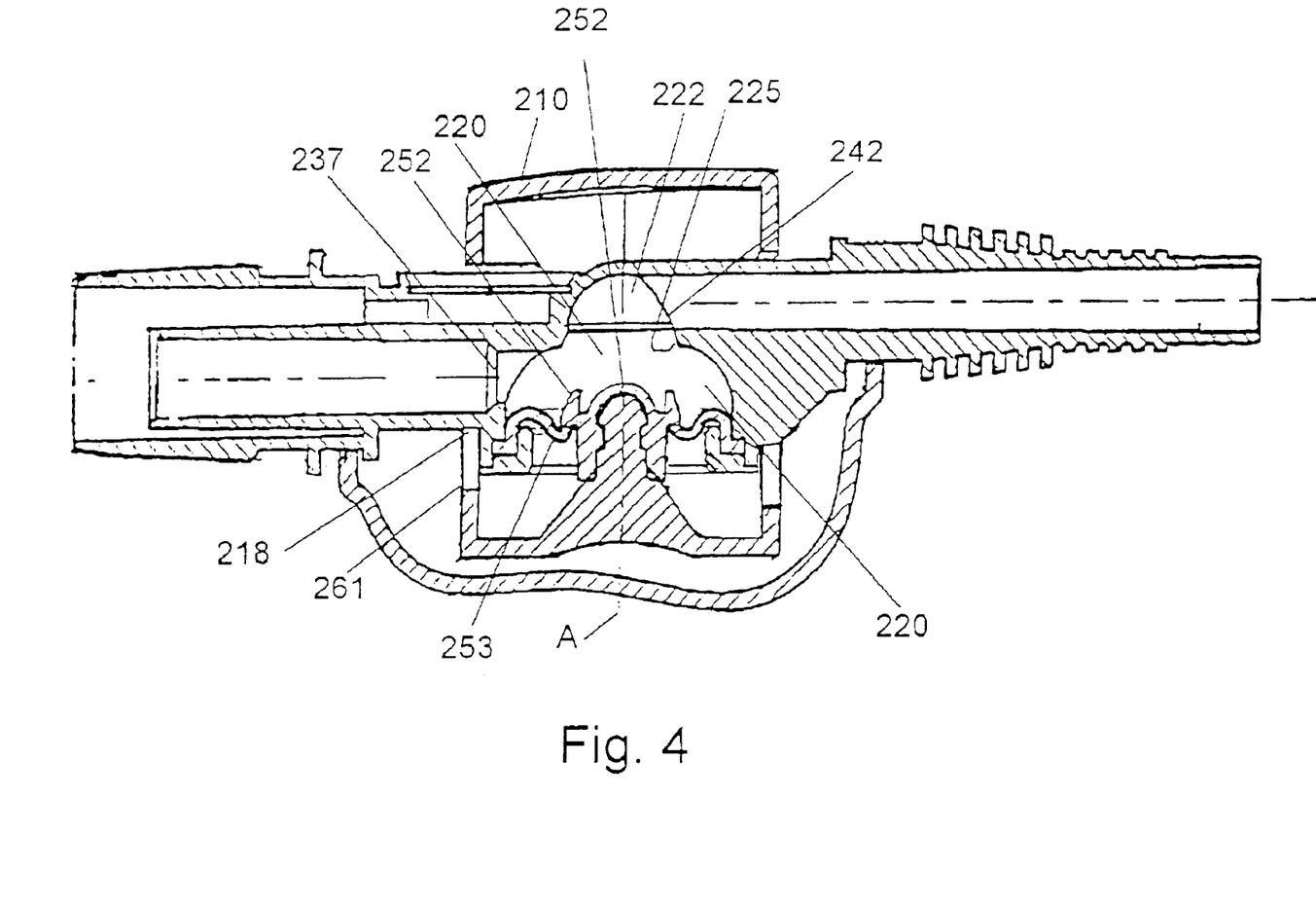
FIGS. 4 and 5 illustrate a part of the valve device shown in FIG. 2, in an open and closed position of the valve body, respectively.
Figure 5:
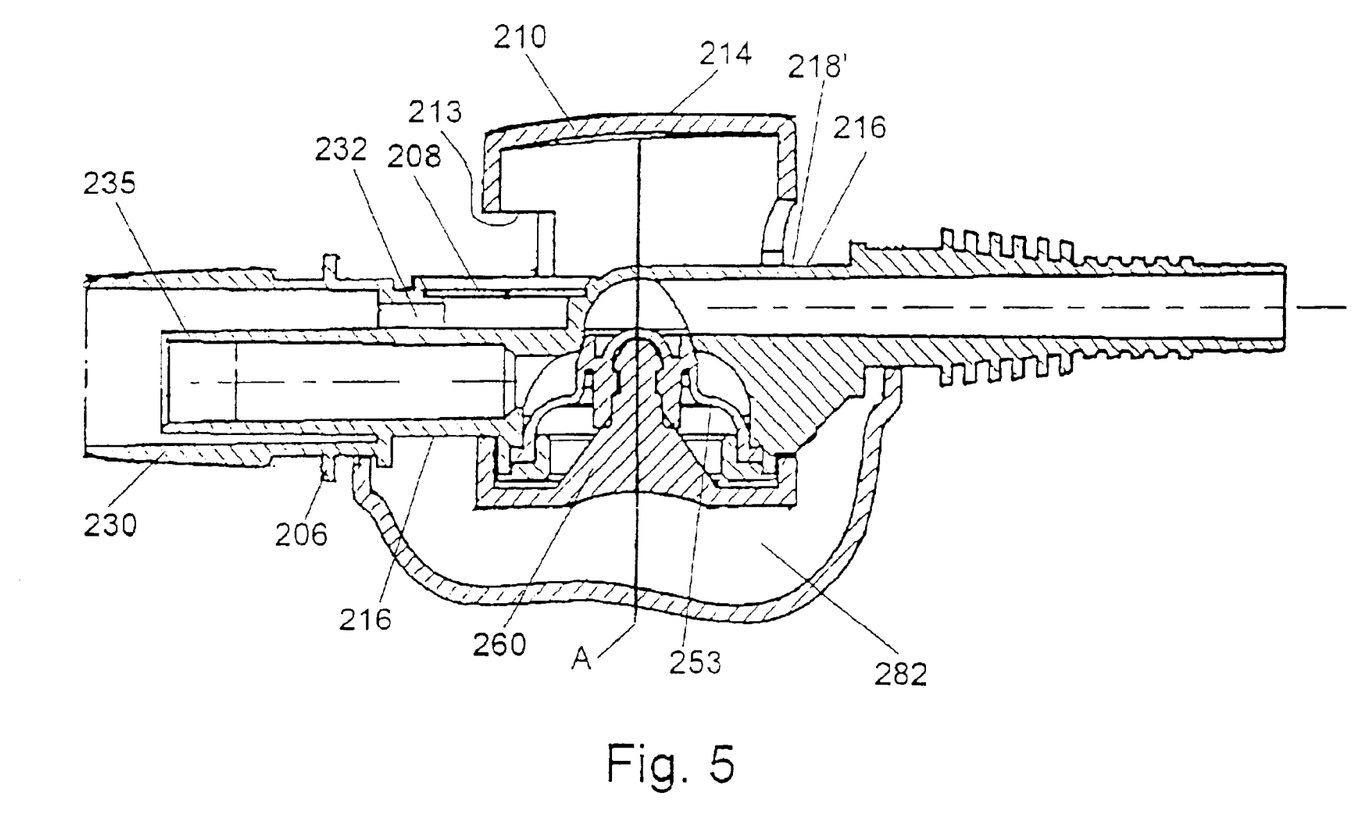

Reference is now made to FIGS. 4 and 5 that show the valve 250 in a first and a second extreme position, respectively, of the valve body 252. For the sake of simplicity the figures show the valve device 200 without the upper half 275 of the actuator housing 270.

In the position of the valve 250 shown in FIG. 4, the valve body 252 is offset downwards along the axis A, ie away from the valve seat 225 of the valve housing 215 that is formed at the transition between the lower cavity 220 and the upper cavity 222. This shifting movement is possible, the cup-shaped portion 253 of the valve 250 being flexible and able to occupy the position outlined in FIG. 4, in which the necessary tensions have been accumulated within the cup-shaped portion 253 that seeks to bring the valve body 252 into abutment on the valve seat 225.

As mentioned previously, the actuator button 210 as well as the coupling means 260 has respective bottom edges 213, 261 that form delimitations for the movements of the actuator button 210 and the coupling means 260, respectively, along the axis A. It will be understood that the bottom edge 213 is arranged such that the user is able to depress the actuator button 210 to such extent that the valve body 252 is to a wide extent caused to completely exit the flow path for fluid that flows through the cavities 220, 222, as the strength and flexibility of the second portion 253 of the valve body 250 being adjusted in accordance with this maximal movement along the axis A. Conversely, the bottom edge 261 on the coupling means 260 will preferably be configured to abut on an area 218 of the valve housing 215 in the closing position of the valve body 250. Hereby it is ensured that the valve body 252 abuts on the valve seat 225 with a certain impact force, a complete relief of the internal stresses in the portion 253 of the valve 250 being avoidable.

It is an important feature of the invention that the coupling means 260 that connects the valve 250 to the actuator button 210 extends outside the cavities 220, 222, ie outside the valve housing 215 proper. Thereby unimpeded flow of fluid through the valve device 200 is ensured. It is concurrently observed that a sub-atmospheric pressure at the tubular member 240 will impart auto-sealing properties to the valve device 200, the sub-atmospheric pressure entailing—when the valve 250 is in the closed position shown in FIG. 5—an increased sealing between the valve body 252 and the valve seat 225.

FIG. 5 illustrates the second state of the valve 250, in which state the valve body 252 abuts on the valve seat 225. From this drawing it will appear that, within the space between the first tubular member 235 and the third tubular member 230, a narrow passage 232 is formed that is configured for connecting the interior of the shrouding 50 with the open. Preferably the passage 232 debouches in a filter 208 that serves to ensure separation of hazardous substances, if any, contained in the air within the shrouding. The passage allows repression and aspiration of air into the shrouding 50 when the shrouding is collapsed and expanded, respectively, during use of the catheter 40. Thus, the air is able to pass along the path shown by the line L in FIG. 2. FIG. 5 also shows the valve device 200 without the securing sleeve 205 shown in FIG. 2 by which the shrouding 50 can be secured around the tubular member 230. The securing sleeve 205 is more specifically clipped in place on the tubular member via a mounting flange 206, and the shrouding is secured by frictional engagement between the surfaces of the securing sleeve 205 and the tubular member 230.

It will be understood from the above that a user of the valve device will first open the lid portion 272 and thus hold the palm of his hand around the lower half 280 of the actuator housing. To allow flow of fluid through the valve device 200 the user subsequently depresses the actuator button 210 until the bottom edge 213 abuts on the surface of the valve housing 215 in an area 218'.

What is claimed is:

1. A valve device for a closed system for endotracheal aspiration of a patient via a catheter, said valve device comprises:
    a wall with an opening and a valve received in said opening, said wall and said valve together defining a valve housing and said valve being adapted to seal said opening;
    a first flow passage, whereby said valve housing can be connected to said catheter;
    a second flow passage, whereby said valve housing can be connected to a vacuum source;
    said valve having a valve body movable within said valve housing along an axis from a first position engaging a valve seat formed opposite said opening, in said first position the first and the second flow passages are separated from each other, to a second position wherein said first and said second flow passages are connected to each other;
    a manually operated actuator button for the valve, wherein said actuator button is configured for being movable between a first position and a second position;
    a coupling engaging said valve body and said actuator button for transmitting said movement of the actuator button to the valve, said coupling extending exteriorly relative to the valve housing;
    said valve including a flexible membrane which spans over said opening and which is connected to said valve body and the wall, respectively, and
    a spring device acting on said valve body,
    wherein said valve body is located closer to said opening in said second position, said flexible membrane permitting said movement of said valve body towards said opening to connect said first and said second flow passages, and
    wherein said spring device is adapted to bias said valve body towards said first position.

2. A valve device according to claim 1, wherein said actuator button is arranged at a first side of said valve housing; and
    said coupling is arranged at an opposite side of the valve housing.

3. A valve device according to claim 2, further comprising an actuator housing enclosing said valve housing and said coupling; and
    said actuator housing further comprises an access opening that allows access to the actuator button.

4. A valve device according to claim 1, wherein said flexible membrane forms said spring device.

5. A valve device according to claim 1, wherein said valve body further comprises a cavity with first engagement means, said cavity facing away from the interior of said valve housing;
    that said coupling further comprises a pin-like member having second engagement means configured for cooperating with said first engagement means.

6. A valve device according to claim 1, wherein said valve housing further comprises a first valve chamber formed as a domed cavity and a second valve chamber formed as a domed cavity and said second valve chamber is located above said first valve chamber;
    said first and said second chamber are rotationally symmetrical relative to the axis;
    said first chamber debouches in said opening; and
    the transition between said first and said second chamber forms said valve seat.

7. A valve device according to claim 6, wherein said first flow passage is configured for debauching in said first chamber; and
    said second flow passage is configured for debouching in said second chamber.

8. A valve device according to claim 1, wherein said coupling and said actuator button are integrally formed.

9. A valve device according to claim 1, wherein a third flow passage encloses said first flow passage;
    said wall also defines a passage that debouches, at a first end, in said third flow passage, and that debouches into the open.

10. A valve device according to claim 9, wherein said passage further comprises a filter means.

11. A valve device according to claim 2, wherein said flexible membrane forms said spring device.

12. A valve device according to claim 3, wherein said flexible membrane forms said spring device.

* * * * *

UNITED STATES PATENT AND TRADEMARK OFFICE
CERTIFICATE OF CORRECTION

PATENT NO. : 6,811,142 B2  
DATED : November 2, 2004  
INVENTOR(S) : Gunnar N. Svendsen It is certified that error appears in the above-identified patent and that said Letters Patent is hereby corrected as shown below:

<u>Column 6,</u>
Lines 4, 7 and 21, "the" should read -- said --.
Line 49, "debauching" should read -- debouching --.

Signed and Sealed this

Seventeenth Day of May, 2005

JON W. DUDAS
*Director of the United States Patent and Trademark Office*